(12) United States Patent
Okazaki (10) Patent No.: US 9,801,659 B2
(45) Date of Patent: Oct. 31, 2017

(54) MEDICAL DEVICE

(71) Applicant: OLYMPUS CORPORATION, Tokyo (JP)

(72) Inventor: Yoshiro Okazaki, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 315 days.

(21) Appl. No.: 14/681,565

(22) Filed: Apr. 8, 2015

(65) Prior Publication Data

US 2015/0209079 A1    Jul. 30, 2015

Related U.S. Application Data

(63) Continuation of application No. PCT/JP2013/075055, filed on Sep. 17, 2013.

(30) Foreign Application Priority Data

Nov. 13, 2012   (JP) .................................. 2012-249518

(51) Int. Cl.
*A61B 17/34*   (2006.01)
*A61B 17/00*   (2006.01)

(52) U.S. Cl.
CPC ...... *A61B 17/3478* (2013.01); *A61B 17/3496* (2013.01); *A61B 2017/00044* (2013.01);
(Continued)

(58) Field of Classification Search
CPC ............ A61B 17/3496; A61B 17/3478; A61B 2017/00044; A61B 2017/00247; A61B 2017/00544; A61B 2017/00703
See application file for complete search history.

(56) References Cited

U.S. PATENT DOCUMENTS 5,738,680 A * 4/1998 Mueller ................ A61B 18/24
606/15
6,224,617 B1   5/2001 Saadat et al.
(Continued)

FOREIGN PATENT DOCUMENTS

JP       2011-078525 A    4/2011
WO   WO 2011/130456 A1   10/2011

OTHER PUBLICATIONS

International Search Report dated Dec. 10, 2013 issued in PCT/JP2013/075055.
(Continued)

*Primary Examiner* — Ashley Fishback
(74) *Attorney, Agent, or Firm* — Scully, Scott, Murphy & Presser, P.C.

(57) ABSTRACT

A medical device is provided. The medical device includes a puncture needle that is inserted into body tissue from outside a body and pierces membranous tissue near pulsating tissue inside the body tissue; a tubular protection member that is disposed on the outer side of the puncture needle; a pulse-information acquisition portion that acquires pulse information of the pulsating tissue; and a driving unit that moves the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts.

4 Claims, 12 Drawing Sheets

(52) U.S. Cl.
CPC .......... *A61B 2017/00247* (2013.01); *A61B 2017/00544* (2013.01); *A61B 2017/00703* (2013.01)

(56) References Cited

U.S. PATENT DOCUMENTS

| | | |
|---|---|---|
| 6,723,082 B1 | 4/2004 | Payne et al. |
| 2006/0247672 A1 | 11/2006 | Vidlund et al. |
| 2008/0208184 A1 | 8/2008 | Davies |
| 2008/0221440 A1 | 9/2008 | Iddan et al. |
| 2009/0171304 A1 | 7/2009 | Cao et al. |
| 2010/0274129 A1 | 10/2010 | Hooven |
| 2012/0088964 A1 | 4/2012 | Gambhir et al. |
| 2012/0095434 A1 | 4/2012 | Fung et al. |
| 2012/0191090 A1 | 7/2012 | Sugahara et al. |

OTHER PUBLICATIONS

Extended Supplementary European Search Report dated May 12, 2016 in related European Application No. 13 85 4284.0.

\* cited by examiner

MEDICAL DEVICE

CROSS-REFERENCE TO RELATED APPLICATIONS

This is a continuation of International Application PCT/JP2013/075055, with an international filing date of Sep. 17, 2013, which is hereby incorporated by reference herein in its entirety. This application claims the benefit of Japanese Patent Application No. 2012-249518, the content of which is incorporated herein by reference.

TECHNICAL FIELD

The present invention relates to medical devices.

BACKGROUND ART

In a known conventional treatment for ventricular tachycardia in which an ablation catheter is percutaneously inserted between the heart and the pericardium (pericardial cavity), an access route through which the ablation catheter is inserted into the pericardial cavity from outside the body is provided by using a puncture needle (for example, see PTL 1).

This puncture needle is inserted into tissue under X-ray observation, and a distal end of the puncture needle is projected into the pericardial cavity and is deformed due to the resilience of a spring that is released when the puncture needle has passed through the pericardium.

Because the pericardium itself cannot be seen in X-ray images and the outline of the heart is unclear, it is impossible to directly determine whether or not the pericardium has been pierced in X-ray images. However, by using the above-described puncture needle, deformation of the distal end of the puncture needle can be observed in X-ray images, and thus, it is possible to determine that the puncture needle has penetrated through the pericardium.

CITATION LIST

Patent Literature

{PTL 1} Japanese Unexamined Patent Application, Publication No. 2011-078525

SUMMARY OF INVENTION

Technical Problem

Because piercing of the pericardium with the puncture needle is performed while the heart is beating, when the heart expands, at which time the distance between the pericardium and the cardiac muscle is extremely small, it is difficult to pierce only the pericardium, without making the tip of the puncture needle contact the cardiac muscle.

A medical device capable of piercing membranous tissue that is difficult to see under X-ray observation, without making a tip contact pulsating tissue adjacent to the membranous tissue is provided.

Solution to Problem

An aspect of the present invention provides a medical device including a puncture needle that is inserted into body tissue from outside a body and pierces membranous tissue near pulsating tissue inside the body tissue; a tubular protection member disposed on the outer side of the puncture needle; a pulse-information acquisition portion that acquires pulse information of the pulsating tissue; and a driving unit that moves the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts.

Another aspect of the present invention provides a medical device including a tubular puncture needle that is inserted into body tissue from outside a body and pierces membranous tissue near pulsating tissue inside the body tissue; a rod-shaped protection member disposed inside the puncture needle; a pulse-information acquisition portion that acquires pulse information of the pulsating tissue; and a driving unit that moves the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts.

The above-described aspects may be configured such that the pulse-information acquisition portion acquires an electrocardiographic waveform, serving as pulse information, and such that the driving unit causes the puncture needle to project out of a distal end opening in the protection member in a period between an S wave and a T wave in the electrocardiographic waveform acquired by the pulse-information acquisition portion.

Furthermore, the above-described aspects may be configured such that the medical device further includes a mode switching portion that switches among a relative movement mode in which the driving unit moves the puncture needle and the protection member relative to each other, a puncture mode in which the tip of the puncture needle is kept projected out of the distal end opening in the protection member, and a protection mode in which the tip of the puncture needle is kept retracted in the distal end opening in the protection member.

Furthermore, the above-described aspects may be configured such that the pulse-information acquisition portion detects a cardiac potential, serving as the pulse information, in the vicinity of the tip of the puncture needle, and the mode switching portion switches the operating mode from the puncture mode to the relative movement mode when the cardiac potential detected by the pulse-information acquisition portion exceeds a predetermined threshold.

Furthermore, the above-described aspects may be configured such that the medical device further includes a biological information detecting unit that detects biological information in the vicinity of the tip of the puncture needle, and the mode switching portion switches the operating mode from the relative movement mode to the protection mode when the biological information detected by the biological information detecting unit shows that the puncture needle has penetrated through the membranous tissue.

The above-described aspects may be configured such that the biological information is one of the pressure, the bioelectrical impedance, the intensity of reflected light, and the puncture resistance.

DESCRIPTION OF EMBODIMENT

A medical device 1 according to an embodiment of the present invention will be described below with reference to the drawings.

Figure 1:
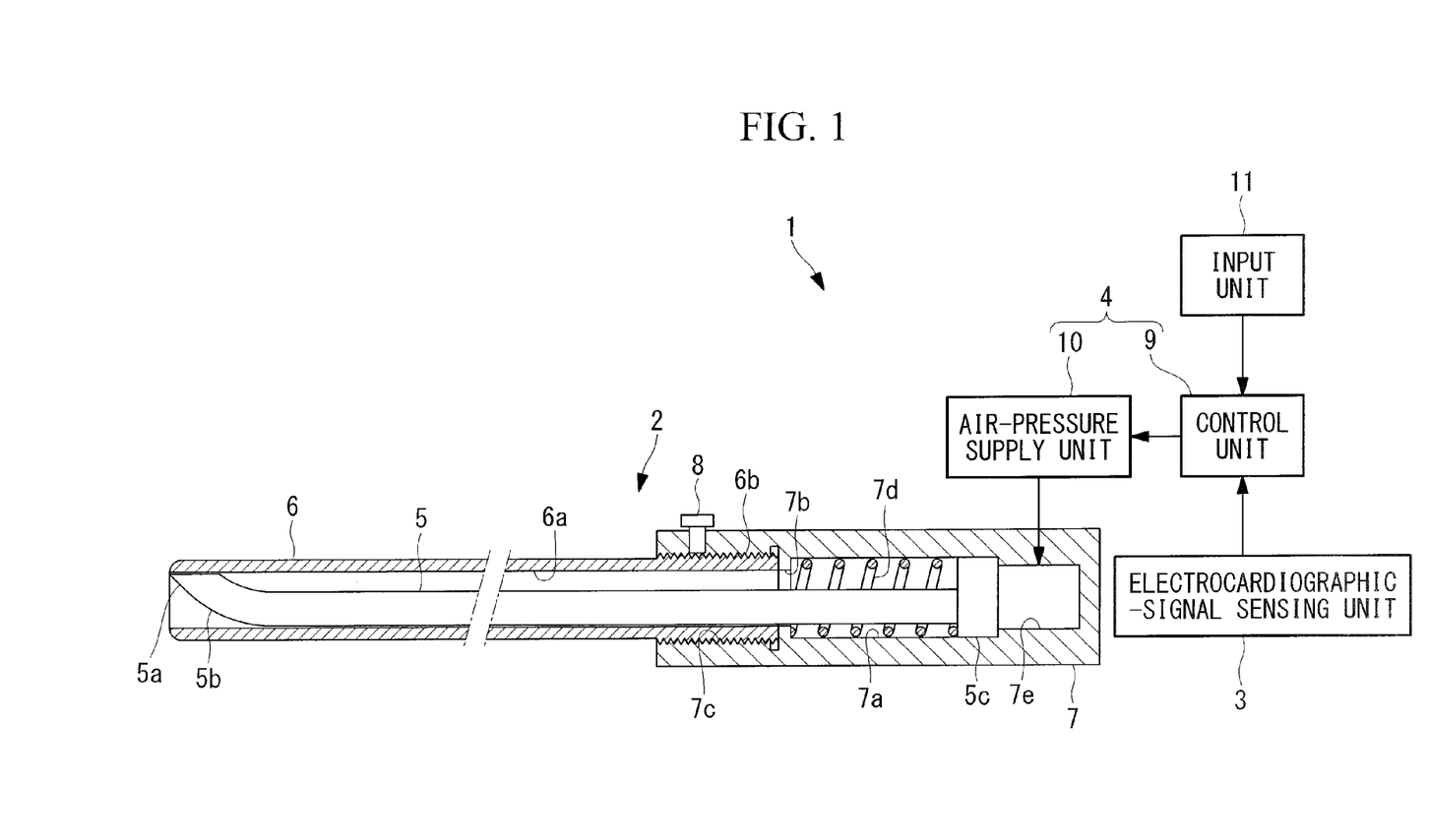
FIG. 1 is a vertical sectional view of a medical device according to an embodiment of the present invention, showing a state in which a puncture needle is retracted.

As shown in FIG. 1, the medical device 1 according to this embodiment includes a device main unit 2, an electrocardiographic-signal sensing unit 3 that detects an electrocardiographic signal, and a driving unit 4 that drives the device main unit 2 on the basis of the electrocardiographic signal detected by the electrocardiographic-signal sensing unit 3.

The device main unit 2 includes a puncture needle 5 that has a tip 5a for piercing body tissue from outside the body of a patient, a cylindrical protection member 6 that has an inside hole 6a that can accommodate the puncture needle 5, and an air-cylinder portion 7 that is joined to the proximal end of the protection member 6 in a removable manner.

The puncture needle 5 has a curved portion 5b, which is curved in one direction, at the distal end thereof, and the curved portion 5b has a sharp tip 5a at the distal end thereof. The puncture needle 5 has a flange portion 5c, which constitutes a piston of the air-cylinder portion 7, at the proximal end thereof.

The protection member 6 has a distal end opening of the inside hole 6a in the unsharpened distal end thereof. The protection member 6 is provided with a male screw 6b at the proximal end.

The air-cylinder portion 7 includes an inside hole 7a in which the flange portion 5c provided on the puncture needle 5 is accommodated so as to be slidable in the longitudinal direction, an inner collar portion 7b projecting radially inward and provided at an intermediate position of the inside hole 7a in the longitudinal direction, a female screw 7c provided in the vicinity of the opening of the inside hole 7a to be engaged with the male screw 6b of the protection member 6, and a compression coil spring 7d disposed between the flange portion 5c and the inner collar portion 7b. The reference sign 8 in the figure denotes a stopper screw.

A sealing member (not shown) is disposed between the flange portion 5c and the inside hole 7a, thus making a portion of the inside hole 7a that is closer to the proximal end than the flange portion 5c is serve as an airtight sealed pressure chamber 7e.

The electrocardiographic-signal sensing unit 3 is, for example, a cardiac electrometer for acquiring a 12-lead electrocardiogram.

The driving unit 4 includes a control unit 9 and an air-pressure supply unit 10 that adjusts the air pressure to be supplied to the pressure chamber 7e on the basis of instruction signals from the control unit 9.

Figure 2:
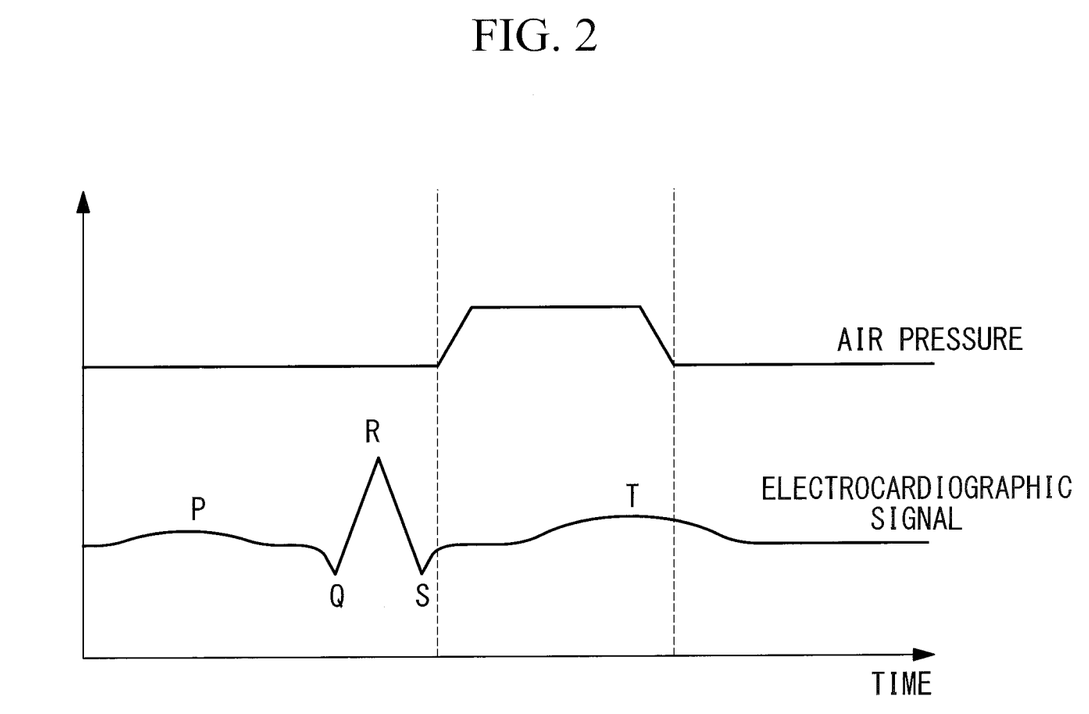
FIG. 2 is a timing chart showing the relationship between the air pressure supplied from an air-pressure supply unit and an electrocardiographic signal, in the medical device in FIG. 1.

The control unit 9 adjusts instruction signals to be fed to the air-pressure supply unit 10 on the basis of the electrocardiographic signal detected by the electrocardiographic-signal sensing unit 3. More specifically, as illustrated in FIG. 2, instruction signals are outputted such that the air pressure supplied to the pressure chamber 7e is increased in a period between the latter half of an S wave and the latter half of a T wave in the electrocardiographic signal and such that the air pressure is decreased in the other period.

The air-pressure supply unit 10 includes an air pressure source (not shown) and a control valve.

Furthermore, in this embodiment, an input unit 11 to be operated by an operator is connected to the control unit 9. The input unit 11 can switch the operating mode of the puncture needle 5, operated by the control unit 9, among three modes.

The three operating modes include a relative movement mode, a puncture mode, and a protection mode.

The relative movement mode is an operating mode in which the control unit 9 causes the puncture needle 5 to reciprocate in the longitudinal direction relative to the protection member 6 in synchronization with an electrocardiographic signal detected by the electrocardiographic-signal sensing unit 3, such that the tip 5a of the puncture needle 5 is projected from and retracted into the distal end of the protection member 6.

Figure 3:
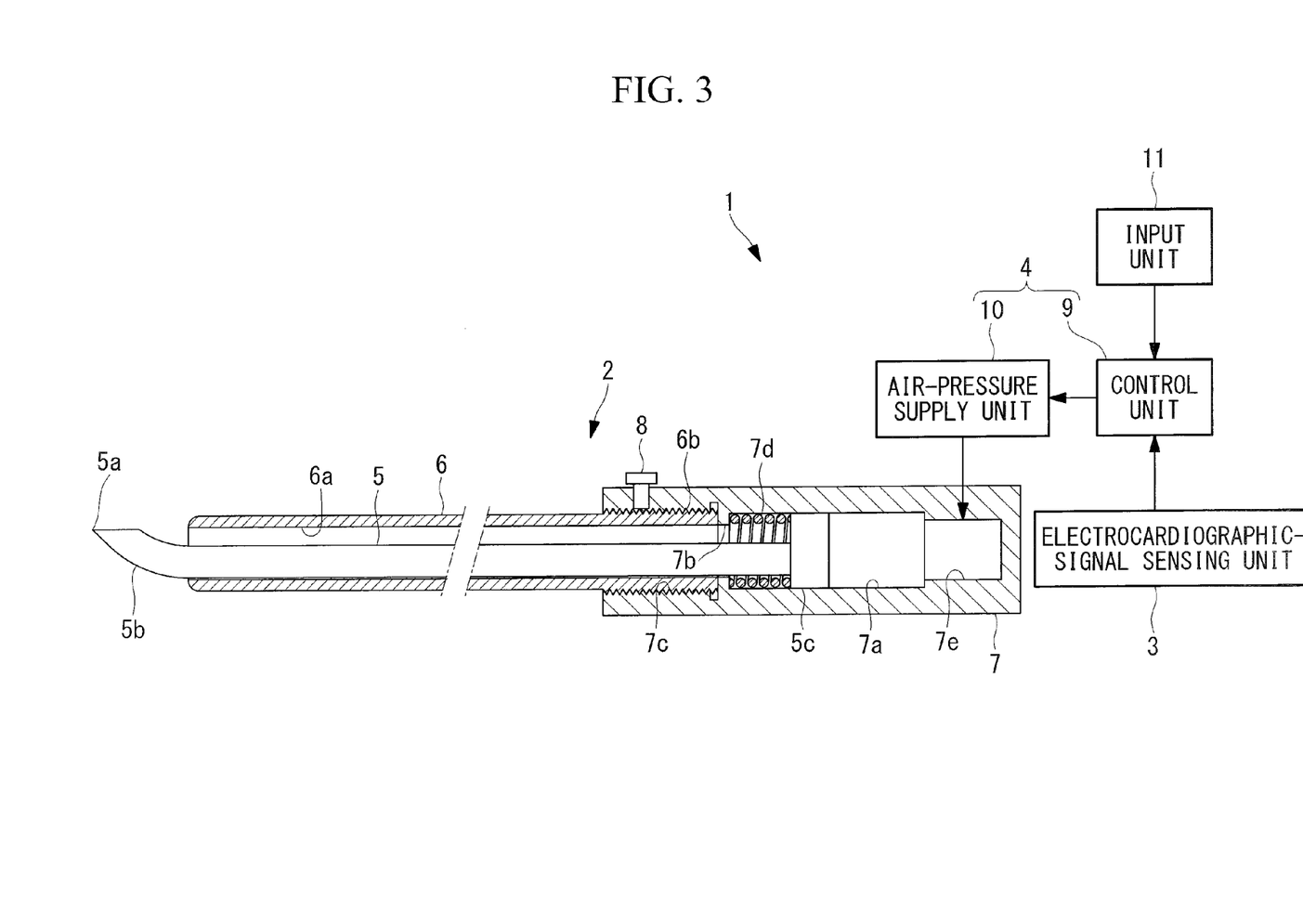
FIG. 3 is a vertical sectional view of the medical device in FIG. 1, showing a state in which the puncture needle is projected out.

The puncture mode is an operating mode in which the puncture needle 5 is not moved in synchronization with the electrocardiographic signal detected by the electrocardiographic-signal sensing unit 3, but the tip 5a of the puncture needle 5 is kept projected farther forward from the distal end of the protection member 6, as illustrated in FIG. 3. More specifically, in the puncture mode, the control unit 9 instructs the air-pressure supply unit 10 to supply high pressure air into the pressure chamber 7e.

The protection mode is also an operating mode in which the puncture needle 5 is not moved in synchronization with the electrocardiographic signal detected by the electrocardiographic-signal sensing unit 3, but the tip 5a of the puncture needle 5 is kept accommodated on the proximal end side of the distal end of the protection member 6, as illustrated in FIG. 1. More specifically, in the protection mode, the control unit 9 instructs the air-pressure supply unit 10 to stop supplying the air pressure into the pressure chamber 7e. When the air pressure drops, the resilience of the compression coil spring 7d pushes back the puncture needle 5 toward the proximal end.

Although an example shown in this embodiment is configured such that the input unit 11 is connected to the control unit 9 and the operating mode of the puncture needle 5 is switched in accordance with the signals from the input unit 11, the input unit 11 and switching of the operating mode are not mandatory.

The operation of the thus-configured medical device 1 according to this embodiment will be described below.

To provide a through-hole for introducing a guide wire into the pericardium A with the medical device 1 according to this embodiment, the input unit 11 is manipulated to select the puncture mode so that the tip 5a of the puncture needle 5 is kept projected from the distal end opening in the protection member 6, as illustrated in FIG. 3.

Figure 4:
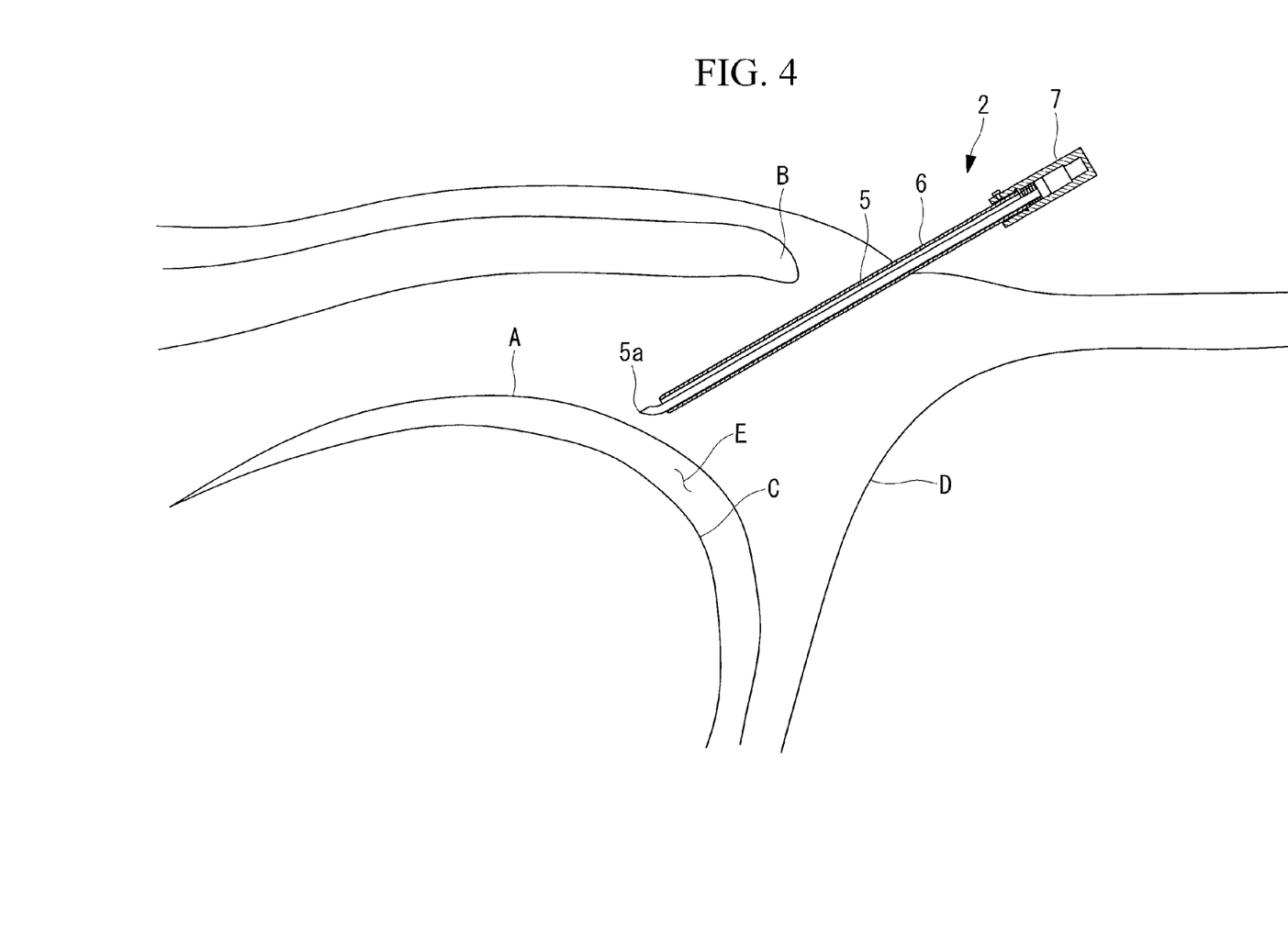
FIG. 4 is a vertical sectional view showing a puncture mode in which a device main unit of the medical device in FIG. 1 is inserted into body tissue from below the xiphisternum.

In this state, as illustrated in FIG. 4, the tip 5a of the puncture needle 5 is inserted into body tissue from a body surface below the xiphisternum B to the vicinity of the heart C under X-ray observation. The reference sign D in the figure denotes a diaphragm.

Next, while the tip 5a is located at a position sufficiently distant from the heart C, the input unit 11 is manipulated to switch the operating mode to the relative movement mode. As a result, the tip 5a of the puncture needle 5 is projected from and retracted into the distal end opening in the protection member 6.

In this state, the insertion motion is continued further. In this operating mode, the tip 5a of the puncture needle 5 is projected from and retracted into the distal end opening in the protection member 6, in synchronization with the electrocardiographic signal. More specifically, the tip 5a is projected from the distal end opening in the protection member 6 between the latter half of the S wave and the latter half of the T wave of the electrocardiographic signal, as illustrated in FIG. 2, and is accommodated in the protection member 6 in the other period.

Because the period between the latter half of the S wave and the latter half of the T wave of the electrocardiographic signal corresponds to a period in which ventricles expel blood into arteries, the cardiac muscle contracts significantly. As a result, the pericardial cavity E between the pericardium A and the heart C expands, increasing the distance between the heart C and the pericardium A.

Figure 5:
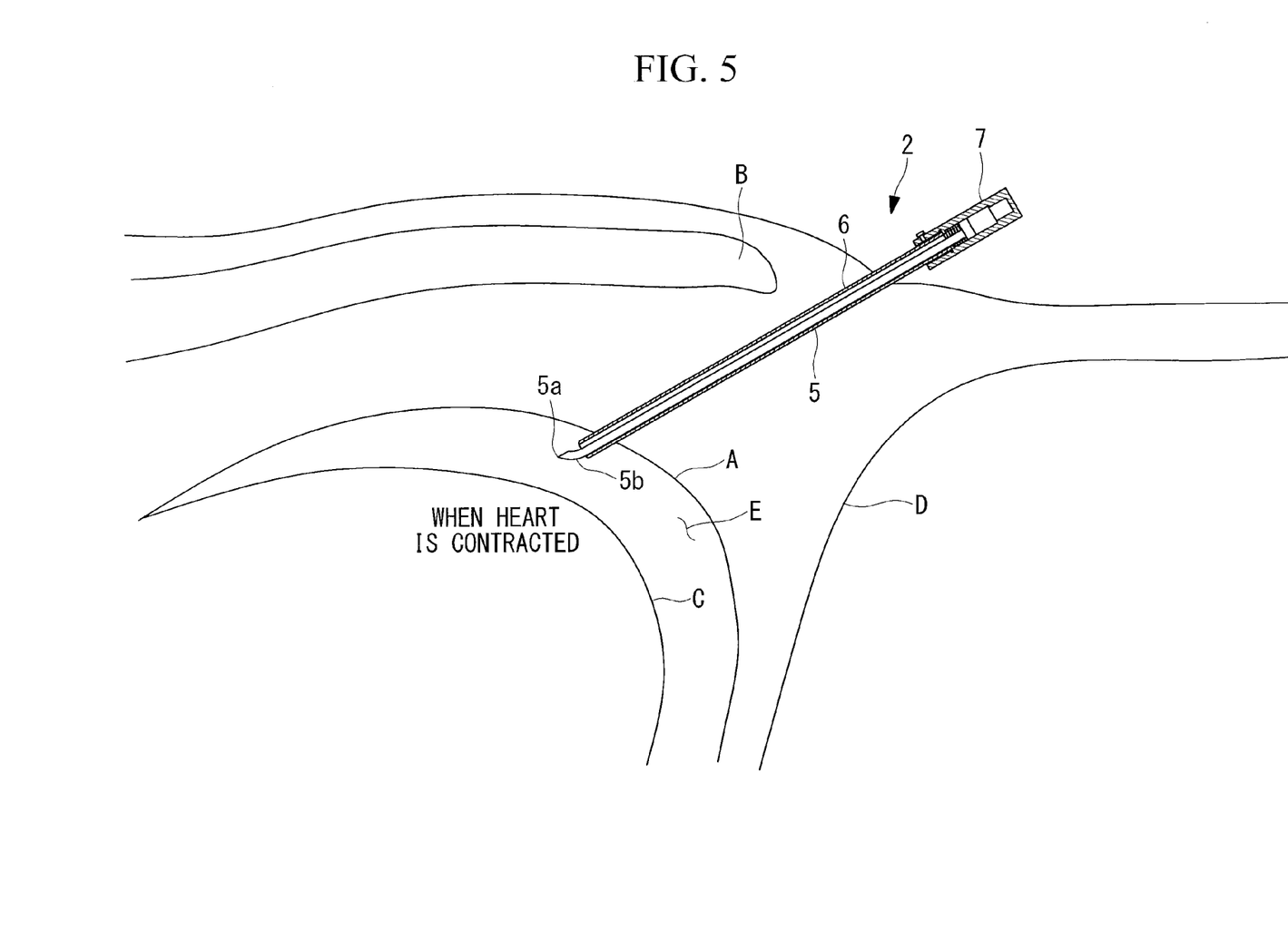
FIG. 5 is a vertical sectional view for describing a relative movement mode when the heart is contracted, showing a state in which the tip of the puncture needle on the device main unit of the medical device in FIG. 1 has penetrated through the pericardium.

Accordingly, when the tip 5a of the puncture needle 5 is projected and passes through the pericardium A during this period, as illustrated in FIG. 5, the risk of the tip 5a contacting the heart C can be sufficiently reduced.

In particular, because the curved portion 5b is provided at the distal end of the puncture needle 5 in this embodiment, if the puncture needle 5 is inserted obliquely into body tissue, as illustrated in FIG. 5, a curved external surface of the curved portion 5b can be made to face the heart C. Thus, even if the puncture needle 5 is projected farther forward from the distal end of the protection member 6 when the heart C expands, contact between the tip 5a of the puncture needle 5 and the heart C can be more reliably avoided.

Figure 6:
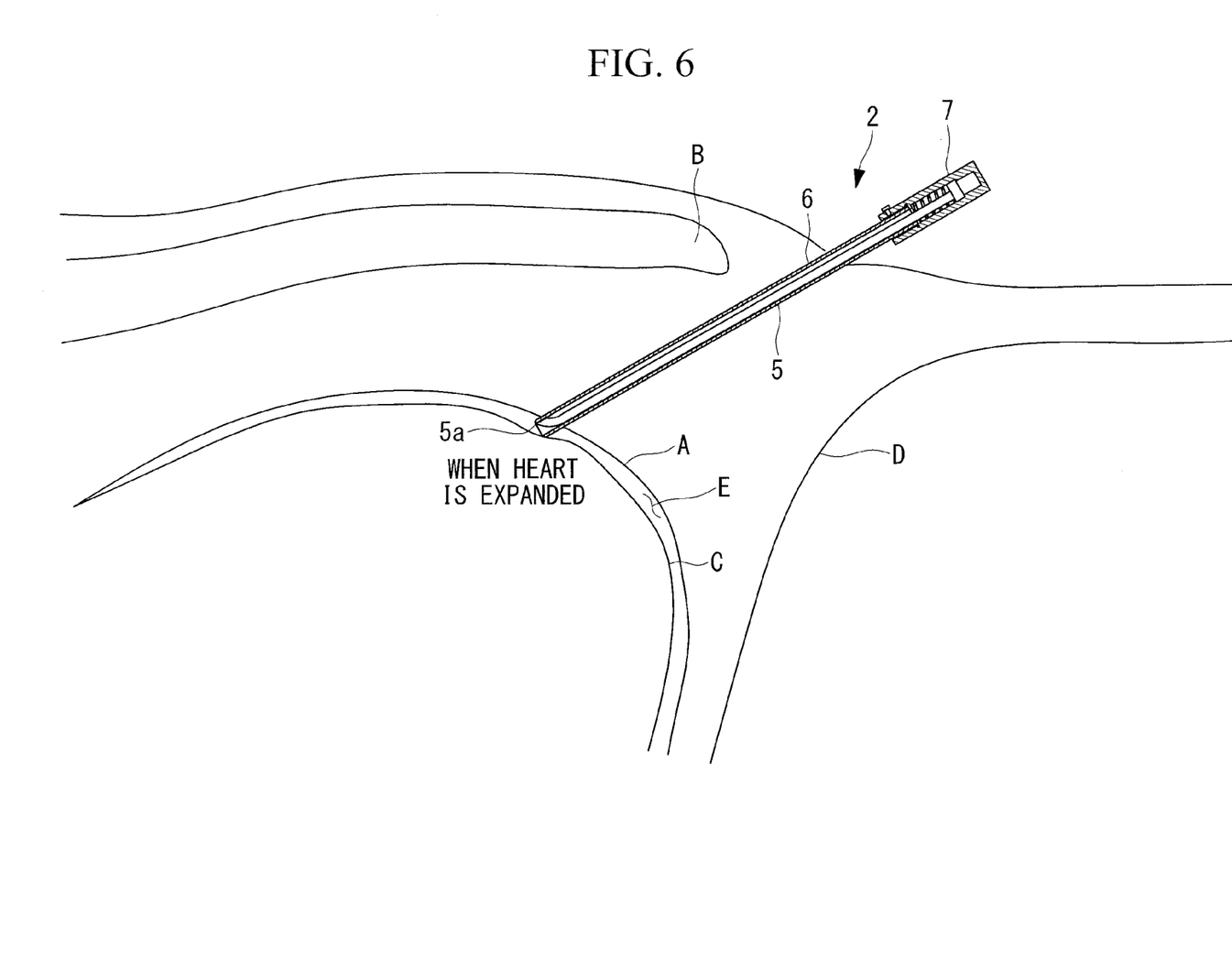
FIG. 6 is a vertical sectional view for describing the relative movement mode when the heart is expanded, showing a state in which the tip of the puncture needle on the device main unit of the medical device in FIG. 1 has penetrated through the pericardium.

On the other hand, in the period other than the period between the latter half of the S wave and the latter half of the T wave of the electrocardiographic signal, the cardiac muscle expands, so, the pericardial cavity E between the pericardium A and the heart C contracts, and the heart C is close to the pericardium A. Therefore, in this period, as illustrated in FIG. 6, by keeping the tip 5a accommodated in the protection member 6 without performing piercing of the pericardium A with the tip 5a of the puncture needle 5, it is possible to reliably prevent the tip 5a of the puncture needle 5 from contacting the heart C.

In other words, by causing the puncture needle 5 to be projected from and retracted into the distal end opening in the protection member 6 in synchronization with the pulse of the heart C, it is possible to pierce the pericardium A, while preventing the tip 5a of the puncture needle 5 from contacting the heart C.

Subsequently, when the pericardium A is pierced, and the distal end of the protection member 6 is inserted into the pericardial cavity E, the operating mode is switched to the protection mode by an input from the input unit 11. By doing so, the tip 5a of the puncture needle 5 is kept accommodated in the protection member 6, and thereafter, the tip 5a of the puncture needle 5 can be reliably prevented from contacting the heart C.

Figure 7:
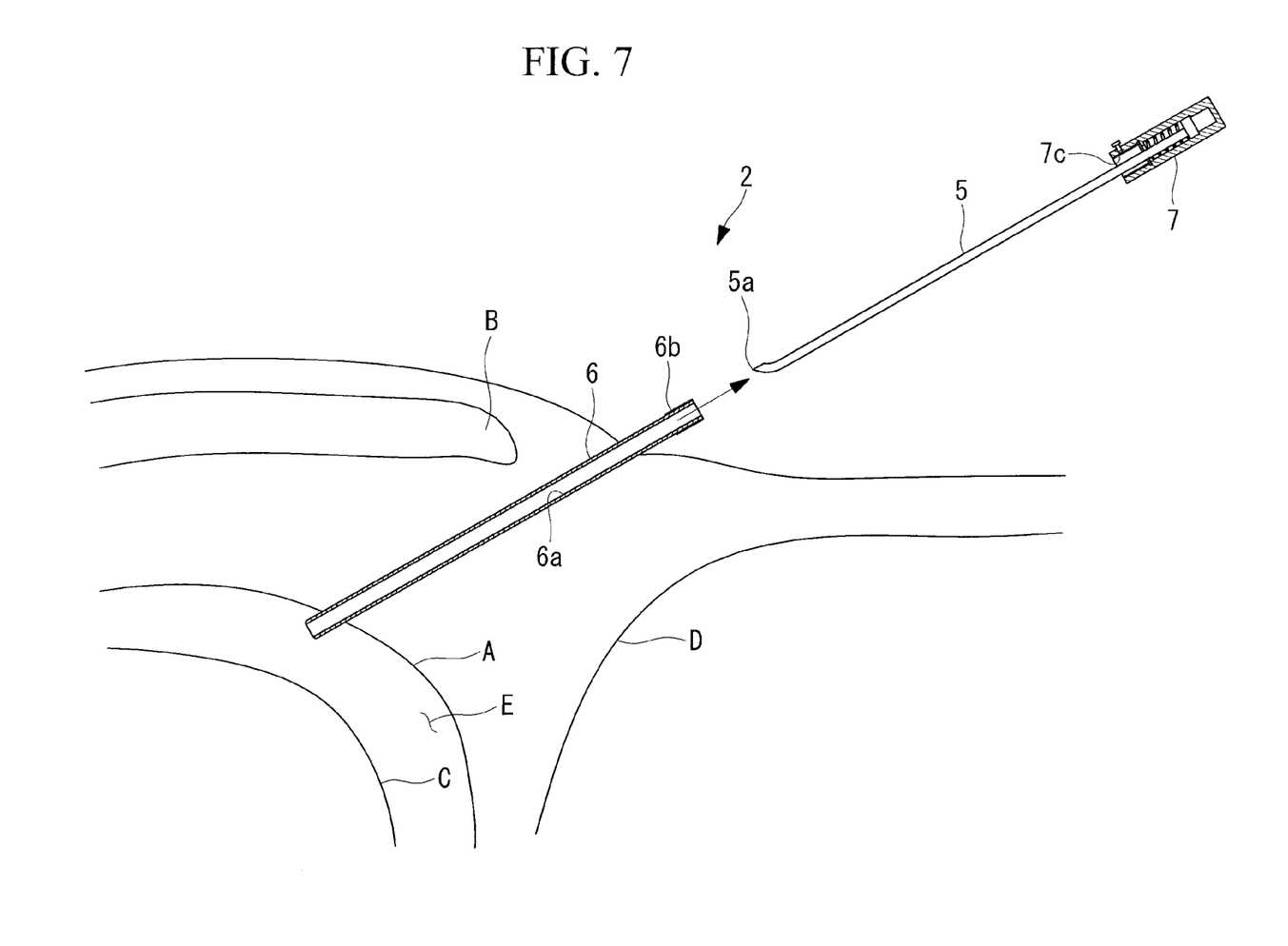
FIG. 7 is a vertical sectional view showing a state in which the puncture needle has been removed from the protection member in the state in FIG. 6.

Then, the stopper screw 8 is loosened to relax fastening between the male screw 6b on the protection member 6 and the female screw 7c in the air-cylinder portion 7, and the air-cylinder portion 7 is removed from the protection member 6, as illustrated in FIG. 7. Then, by pulling the puncture needle 5 out of the inside hole 6a in the protection member 6 toward the proximal end, it is possible to introduce a guide wire (not shown) into the pericardial cavity E through the inside hole 6a in the protection member 6.

As described above, because the medical device 1 according to this embodiment performs piercing of the pericardium A not with the constantly projected puncture needle 5, but with the tip 5a that is projected and retracted in synchronization with the electrocardiographic signal, there is an advantage in that the medical device 1 can pierce the pericardium A while preventing the tip 5a of the puncture needle 5 from contacting the heart C.

Although the puncture needle 5 is moved relative to the protection member 6, as illustrated in FIGS. 1 and 3, in this embodiment, an alternative configuration in which the protection member 6 is moved relative to the puncture needle 5 is also possible.

Figure 8:
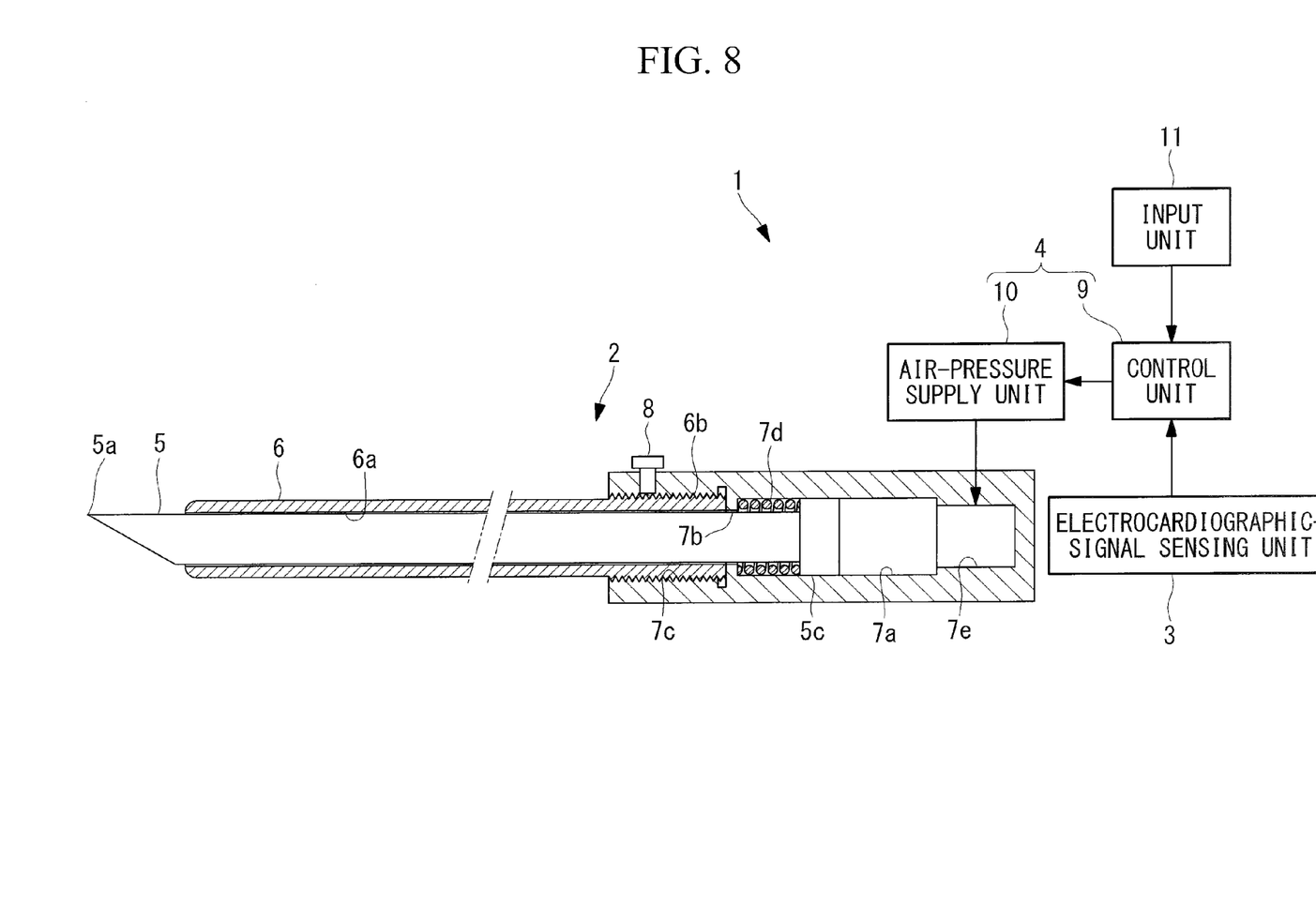
FIG. 8 is a vertical sectional view of a first modification of the medical device in FIG. 1.

Furthermore, although the puncture needle 5 is provided with the curved portion 5b so that contact of the tip 5a with the heart C can be more reliably avoided when the puncture needle 5 is projected farther forward from the distal end of the protection member 6 in this embodiment, an alternative configuration in which a straight puncture needle 5 having no curved portion 5b, as illustrated in FIG. 8, is employed is also possible.

Figure 9:
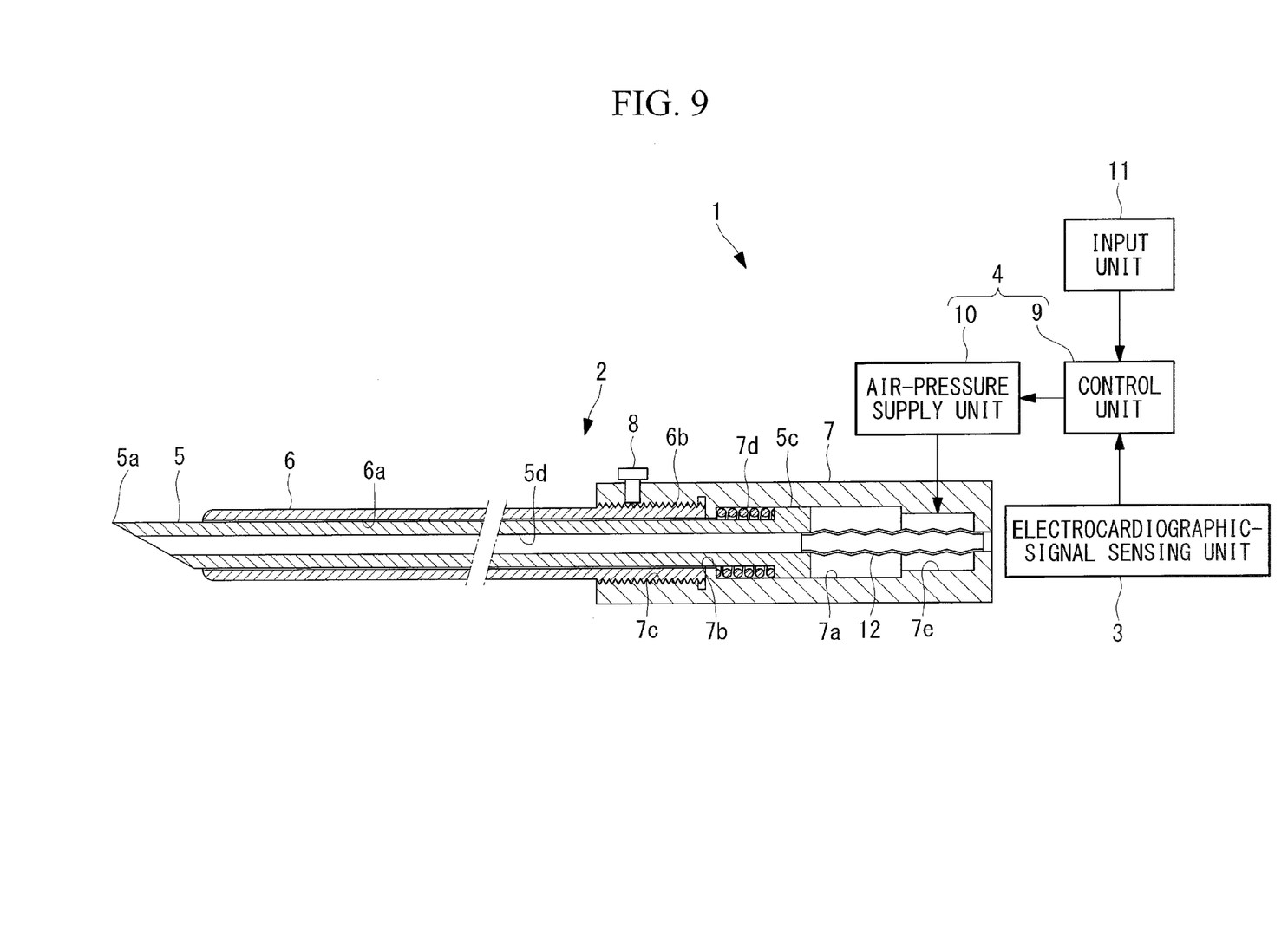
FIG. 9 is a vertical sectional view of a second modification of the medical device in FIG. 1.

Furthermore, although the puncture needle 5 is formed of a solid acicular member in this embodiment, an alternative configuration in which the puncture needle 5 is formed of a hollow tubular member, as illustrated in FIG. 9, is also possible. In such a case, an inside hole 5d of the puncture needle 5 and an end face of the air-cylinder portion 7 at the proximal end may be made to communicate with each other via a tubular member 12 that can be expanded and contracted like a bellows.

With this configuration, it is possible to supply contrast medium from the end face of the air-cylinder portion 7 at the proximal end to the distal end of the puncture needle 5 through the tubular member 12 and the inside hole 5d of the puncture needle 5. By doing so, it is possible to more accurately determine, under X-ray observation, whether or not the tip 5*a* of the puncture needle 5 has entered the pericardial cavity E through the pericardium A.

Furthermore, the use of the above-described configuration provides another advantage in that it is possible to introduce a guide wire into the pericardial cavity E through the tubular member 12 and the inside hole 5*d* of the puncture needle 5 without removing the puncture needle 5 from the protection member 6.

Figure 10:
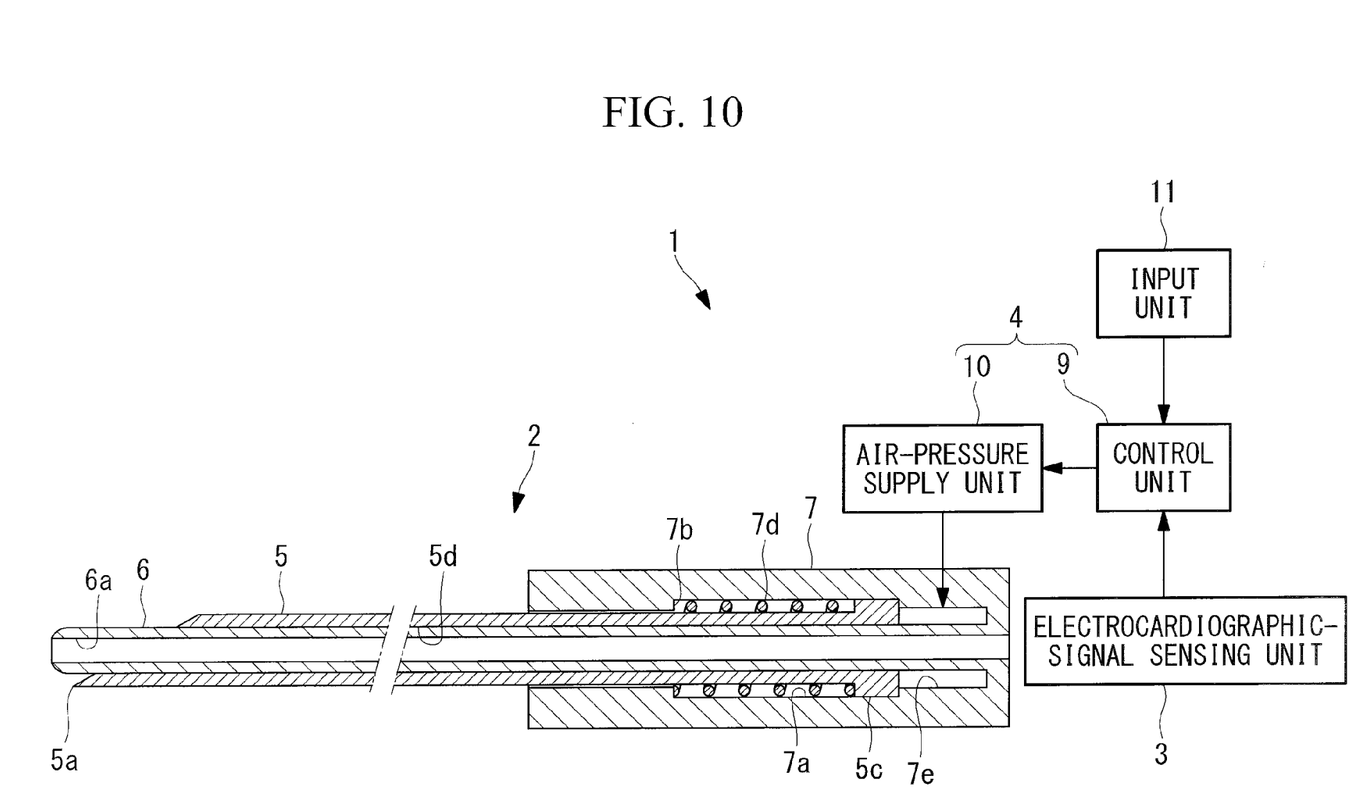
FIG. 10 is a vertical sectional view of a third modification of the medical device in FIG. 1, showing a state in which the puncture needle is retracted.
Figure 11:
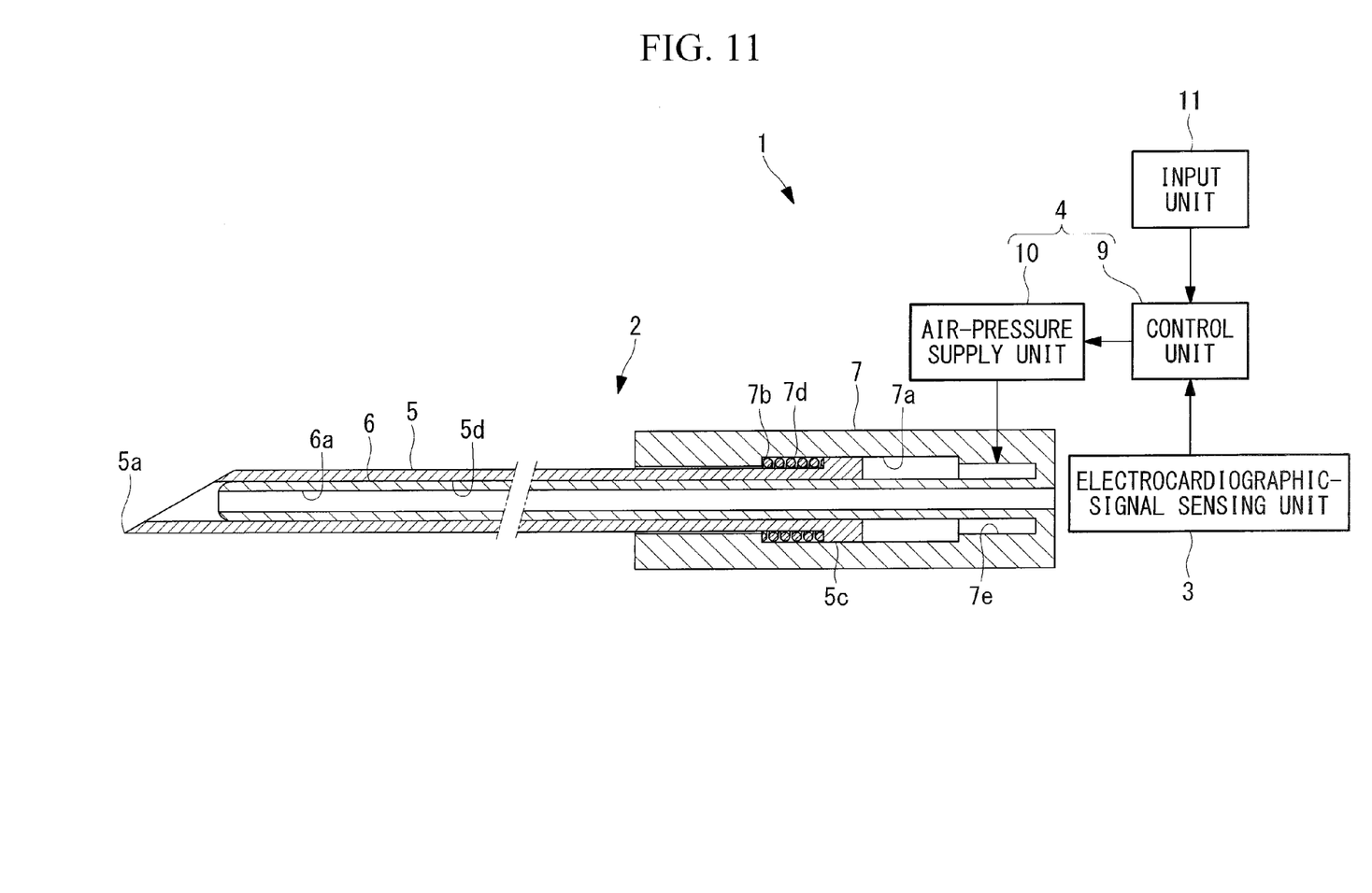
FIG. 11 is a vertical sectional view showing a state in which the puncture needle of the medical device in FIG. 10 is projected out.

Furthermore, although the tubular protection member 6 that can accommodate the puncture needle 5 is disposed on the outer side of the puncture needle 5 in this embodiment, an alternative configuration in which a rod-shaped or tubular protection member 6 is disposed on the inner side of the tubular puncture needle 5 such that they move relative to each other, as illustrated in FIGS. 10 and 11, is also possible.

In the examples shown in FIGS. 10 and 11, the tubular protection member 6 disposed so as to be inserted at the inner side of the puncture needle 5 is fixed to the air-cylinder portion 7, and the tip 5*a* of the puncture needle 5 is located at a position either farther forward or towards the proximal end from the distal end of the protection member 6 due to the air pressure supplied to the pressure chamber 7*e* in the air-cylinder portion 7. Conversely, a configuration in which the puncture needle 5 is fixed and the protection member 6 is advanced or retracted relative to the puncture needle 5 may be employed.

Figure 12:
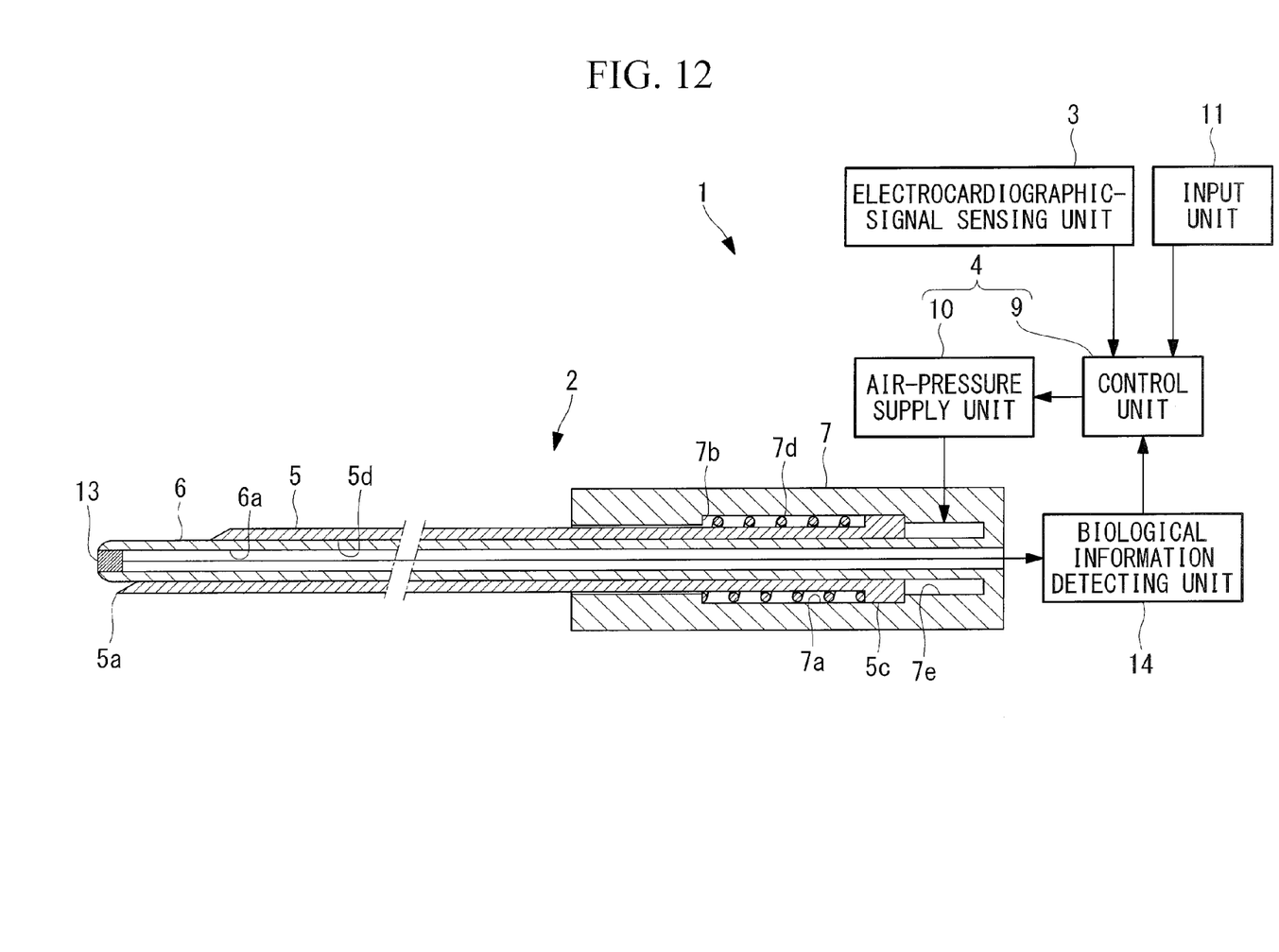
FIG. 12 is a vertical sectional view of a fourth modification of the medical device in FIG. 1.

Furthermore, when the puncture needle 5 or protection member 6 that is disposed on the radially inner side is provided with the inside hole 6*a* extending in the longitudinal direction, the inside hole 6*a* may be used to detect biological information, and such information may be used to switch the operating mode, as illustrated in FIG. 12.

For example, in the example shown in FIG. 12, a pressure sensor, serving as a sensor 13, may be disposed at the distal end of the protection member 6, and biological information may be detected with a biological information detecting unit 14 on the basis of the pressure detected by the sensor 13.

More specifically, the pressure detected by the pressure sensor during piercing of the body tissue and the pericardium A is mainly the pressure received from the tissue. However, once the puncture needle 5 has penetrated through the pericardium A, the pressure in the pericardial cavity E is detected, and the pressure drops. Hence, upon the pressure sensor sensing the pressure in the pericardial cavity E, the relative movement mode can be automatically switched to the protection mode. Note that a change in pressure may be notified externally by lighting a pilot lamp, by an indication on a display, or by voice.

Note that the pressure sensor may be disposed at the proximal end of the inside hole 6*a* in the protection member 6, instead of at the distal end of the protection member 6. In such a case, the operating mode may be switched upon sensing change in pressure in the inside hole 6*a*.

Furthermore, for example, in the example shown in FIG. 12, an electrode for measuring the bioelectrical impedance, serving as biological information, may be provided as the sensor 13.

Because the bioelectrical impedance differs between when the body tissue or the pericardium A is in contact with the electrode and when the electrode is disposed in a space inside the pericardial cavity E, the relative movement mode can be automatically switched to the protection mode upon detection of a change in bioelectrical impedance, similarly to the case of the pressure.

Furthermore, for example, in the example shown in FIG. 12, a light sensor that irradiates a target with light and detects scattered returning light as biological information may be employed as the sensor 13.

The intensity of scattered light returning from the tissue is high during piercing of the body tissue or the pericardium A with the puncture needle 5. However, once the puncture needle 5 has penetrated through the pericardium A, the light is radiated onto the large pericardial cavity E, so, the intensity of reflected light detected drops. Therefore, when the intensity of light detected by the light sensor drops, the relative movement mode can be automatically switched to the protection mode.

Furthermore, for example, in the example shown in FIG. 1, the puncture needle 5 may be formed of a conducting material, and by connecting a cardiac electrometer to the puncture needle 5, the puncture needle 5 may be used as an electrode for sensing the cardiac potential.

Because a relatively large electric current flows when the puncture needle 5 contacts the pericardium A, the detected cardiac potential changes considerably. Thus, by sensing this change in cardiac potential, it may be determined that the puncture needle 5 contacted the pericardium A. That is, by sensing a change in cardiac potential, the puncture mode can be automatically switched to the relative movement mode.

Furthermore, by sensing a change in pressure in the pressure chamber 7*e* with a pressure sensor or by sensing puncture resistance transmitted through the puncture needle 5 with a load cell (not shown), instead of sensing the pressure using the inside hole 6*a* in the protection member 6, a force applied to the puncture needle 5 during puncture may be detected directly and utilized to switch the operating mode. More specifically, the pressure in the pressure chamber 7*e* and the puncture resistance applied to the puncture needle 5 are high during piercing of the body tissue with the projected puncture needle 5, whereas they drop when the puncture needle 5 has penetrated through the pericardium A. Hence, the operating mode may be automatically switched to the protection mode when such a drop in pressure or a drop in puncture resistance is detected.

Although the heart C and the pericardium A have been described as an example of pulsating tissue and membranous tissue, respectively, in this embodiment, the pulsating tissue and the membranous tissue are not limited thereto.

Furthermore, although the electrocardiographic signal has been described as an example of pulse information, the pulse information is not limited thereto.

The above-described embodiment leads to the following inventions.

An aspect of the present invention provides a medical device including a puncture needle that is inserted into body tissue from outside a body and pierces membranous tissue near pulsating tissue inside the body tissue; a tubular protection member disposed on the outer side of the puncture needle; a pulse-information acquisition portion that acquires pulse information of the pulsating tissue; and a driving unit that moves the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts.

According to this aspect, the puncture needle of the medical device, in a state projected from the protection member, is inserted into the body tissue from outside the body, and, before reaching the membranous tissue near the pulsating tissue, the driving unit is activated to move the puncture needle and the protection member relative to each other, thereby causing the tip of the puncture needle to be projected from and retracted into the distal end of the protection member.

The driving unit moves the puncture needle and the protection member relative to each other in synchronization with the pulse information acquired by the pulse-information acquisition portion. Hence, when the pulsating tissue expands, i.e., when the surface of the pulsating tissue moves in a direction toward the puncture needle, contact between the tip of the puncture needle and the pulsating tissue can be avoided by moving the tip of the puncture needle in a direction retracted to the proximal end side of the distal end of the protection member.

On the other hand, when the pulsating tissue contracts, i.e., when the surface of the pulsating tissue moves in a direction away from the adjacent membranous tissue, the membranous tissue can be pierced with the tip of the puncture needle by projecting the tip of the puncture needle farther forward from the distal end of the protection member. In this case, since the pulsating tissue is away from the membranous tissue because of the contraction of the pulsating tissue, the membranous tissue can be more reliably pierced without the tip of the puncture needle contacting the pulsating tissue.

Another aspect of the present invention provides a medical device including a tubular puncture needle that is inserted into body tissue from outside a body and pierces membranous tissue near pulsating tissue inside the body tissue; a rod-shaped protection member disposed inside the puncture needle; a pulse-information acquisition portion that acquires pulse information of the pulsating tissue; and a driving unit that moves the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts.

The above-described aspects may be configured such that the pulse-information acquisition portion acquires an electrocardiographic waveform, serving as pulse information, and such that the driving unit causes the puncture needle to project out of a distal end opening in the protection member in a period between an S wave and a T wave in the electrocardiographic waveform acquired by the pulse-information acquisition portion.

With this configuration, in the case where the pulsating tissue is the heart, because the period between the S wave and the T wave in the electrocardiographic waveform corresponds to a contraction phase of ventricles, the distance between the pericardium, serving as the membranous tissue, and the cardiac muscle is large. Hence, by causing the puncture needle to project out of the distal end opening in the protection member in this period, the pericardium can be pierced without the tip of the puncture needle contacting the cardiac muscle.

Furthermore, the above-described aspects may be configured such that the medical device further includes a mode switching portion that switches among a relative movement mode in which the driving unit moves the puncture needle and the protection member relative to each other, a puncture mode in which the tip of the puncture needle is kept projected out of the distal end opening in the protection member, and a protection mode in which the tip of the puncture needle is kept retracted in the distal end opening in the protection member.

With this configuration, when the mode switching portion is activated to switch the operating mode to the puncture mode, the tip of the puncture needle is kept projected out of the distal end opening in the protection member. Hence, in an area where the risk of the tip of the puncture needle contacting the pulsating tissue is low, continuous piercing of body tissue leading to membranous tissue is possible, with the puncture needle being constantly projected.

On the other hand, when the mode switching portion is activated to switch the operating mode to the protection mode, the tip of the puncture needle is kept accommodated in the distal end opening in the protection member. Hence, after the tip of the puncture needle has penetrated through the membranous tissue, the tip of the puncture needle can be accommodated in the protection member so as not to contact pulsating tissue.

Furthermore, the above-described aspects may be configured such that the pulse-information acquisition portion detects a cardiac potential, serving as the pulse information, in the vicinity of the tip of the puncture needle, and the mode switching portion switches the operating mode from the puncture mode to the relative movement mode when the cardiac potential detected by the pulse-information acquisition portion exceeds a predetermined threshold.

With this configuration, when the cardiac potential in the vicinity of the tip of the puncture needle, detected by the pulse-information acquisition portion, is less than or equal to a predetermined threshold, it is possible to detect that the tip of the puncture needle is located at a position far from the membranous tissue, and when it has exceeded the predetermined threshold, it is possible to detect that the tip of the puncture needle has contacted the membranous tissue. Hence, when the tip of the puncture needle is away from the membranous tissue, the puncture mode is selected to keep the tip of the puncture needle projected from the distal end opening in the protection member to enable continuous piercing of the body tissue, and when the tip of the puncture needle contacts the membranous tissue, the relative movement mode is selected to enable piercing of the membranous tissue while avoiding contact with the pulsating tissue.

Furthermore, the above-described aspects may be configured such that the medical device further includes a biological information detecting unit that detects biological information in the vicinity of the tip of the puncture needle, and the mode switching portion switches the operating mode from the relative movement mode to the protection mode when the biological information detected by the biological information detecting unit shows that the puncture needle has penetrated through the membranous tissue.

With this configuration, when penetration of the membranous tissue by the puncture needle is detected from the biological information detected by the pulse-information acquisition portion in the vicinity of the tip of the puncture needle, the operating mode is switched from the relative movement mode to the protection mode. By doing so, the tip of the puncture needle is accommodated in the distal end opening in the protection member, and the tip can be more reliably prevented from contacting pulsating tissue.

The above-described aspects may be configured such that the biological information is one of the pressure, the bioelectrical impedance, the intensity of reflected light, and the puncture resistance.

With this configuration, it is possible to detect penetration of the membranous tissue, by using one of the pressure, the bioelectrical impedance, the intensity of reflected light, and the puncture resistance as the biological information.

The present invention provides an advantage in that it is possible to pierce membranous tissue that is difficult to see under X-ray observation, without making a tip contact pulsating tissue adjacent to the membranous tissue.

REFERENCE SIGNS LIST

A pericardium (membranous tissue)
C heart (pulsating tissue)
1 medical device
3 electrocardiographic-signal sensing unit (pulse-information acquisition portion)
4 driving unit
5 puncture needle
5a tip
6 protection member
14 biological information detecting unit

The invention claimed is:

1. A medical device comprising:
   a puncture needle that is configured to be inserted into body tissue from outside a body and pierces membranous tissue near pulsating tissue inside the body tissue;
   a tubular protection member disposed on an outer side of the puncture needle;
   a pulse-information acquisition portion configured to acquire pulse information of the pulsating tissue; and
   an air pressure supply configured to move the puncture needle and the protection member relative to each other in synchronization with the pulse information of the pulsating tissue acquired by the pulse-information acquisition portion, in such a manner that a tip of the puncture needle is retracted toward a proximal end from a distal end of the protection member when the pulsating tissue expands and that the tip of the puncture needle is projected farther forward from the distal end of the protection member when the pulsating tissue contracts, further comprising a mode switching portion that switches among a relative movement mode in which the air pressure supply moves the puncture needle and the protection member relative to each other, a puncture mode in which the tip of the puncture needle is kept projected farther forward from the distal end of the protection member, and a protection mode in which the tip of the puncture needle is kept retracted to the proximal end side of the distal end of the protection member, wherein the pulse-information acquisition portion detects a cardiac potential, serving as the pulse information, in the vicinity of the tip of the puncture needle, and the mode switching portion switches an operating mode from the puncture mode to the relative movement mode when the cardiac potential detected by the pulse-information acquisition portion exceeds a predetermined threshold.

2. The medical device according to claim 1, wherein
   the pulse-information acquisition portion is configured to acquire an electrocardiographic waveform, serving as pulse information, and
   the air pressure supply causes the puncture needle to project out of a distal end opening in the protection member in a period between an S wave and a T wave in the electrocardiographic waveform acquired by the pulse-information acquisition portion.

3. The medical device according to claim 1, wherein the air pressure supply receives a detected biological information in the vicinity of the tip of the puncture needle, wherein the mode switching portion switches an operating mode from the relative movement mode to the protection mode when the detected biological information shows that the puncture needle has penetrated through the membranous tissue.

4. The medical device according to claim 3, wherein the detected biological information is one of pressure, bioelectrical impedance, intensity of reflected light, and puncture resistance.

* * * * *